United States Patent
Ito

(10) Patent No.: US 10,562,074 B2
(45) Date of Patent: Feb. 18, 2020

(54) MICROPARTICLE SORTING METHOD AND MICROCHIP FOR SORTING MICROPARTICLES

(71) Applicant: SONY CORPORATION, Tokyo (JP)

(72) Inventor: Tatsumi Ito, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/658,693

(22) Filed: Jul. 25, 2017

(65) Prior Publication Data

US 2017/0320104 A1 Nov. 9, 2017

Related U.S. Application Data

(62) Division of application No. 13/963,188, filed on Aug. 9, 2013, now Pat. No. 9,737,912.

(30) Foreign Application Priority Data

Aug. 16, 2012 (JP) ................. 2012-180317

(51) Int. Cl.
*B07C 5/34* (2006.01)
*F16K 99/00* (2006.01)
*B07C 5/342* (2006.01)

(52) U.S. Cl.
CPC ........... *B07C 5/3416* (2013.01); *B07C 5/342* (2013.01); *F16K 99/0001* (2013.01); *B01L 2300/0819* (2013.01); *B01L 2300/0861* (2013.01); *F16K 99/0028* (2013.01)

(58) Field of Classification Search
CPC .. B07C 5/02; B07C 5/34; B07C 5/342; B07C 5/3416; B07C 5/3425; F16K 99/0001; F16K 99/0028; B01L 2300/0819; B01L 2300/0861; B01L 2300/0864; B01L 2300/0877; B01L 2300/14
USPC ........ 209/552, 576, 577, 586–588, 643, 932
See application file for complete search history.

(56) References Cited

U.S. PATENT DOCUMENTS

| | | | |
|---|---|---|---|
| 8,623,294 B2 | 1/2014 | Asogawa et al. | |
| 2003/0234210 A1 | 12/2003 | Deshpande et al. | |
| 2006/0037915 A1 | 2/2006 | Strand et al. | |
| 2012/0078531 A1 | 3/2012 | Lo et al. | |

FOREIGN PATENT DOCUMENTS

| | | |
|---|---|---|
| CN | 1662311 A | 8/2005 |
| JP | 2005-524831 A | 8/2005 |
| JP | 2005-538727 A | 12/2005 |

(Continued)

OTHER PUBLICATIONS

Non-Final Rejection for U.S. Appl. No. 13/963,188, dated Jul. 6, 2015, 06 pages.

(Continued)

*Primary Examiner* — Charles A Fox
*Assistant Examiner* — Kalyanavenkateshware Kumar
(74) *Attorney, Agent, or Firm* — Chip Law Group

(57) ABSTRACT

There is provided a microparticle sorting method including a procedure of collecting a microparticle in a fluid that flows through a main channel in a branch channel that is in communication with the main channel by generating a negative pressure in the branch channel. In the procedure, a flow of a fluid is formed that flows toward a side of the main channel from a side of the branch channel at a communication opening between the main channel and the branch channel.

14 Claims, 15 Drawing Sheets

1a: MICROCHIP
12: SAMPLE FLUID CHANNEL
14: SHEATH FLUID CHANNEL
16: SORTING CHANNEL
18: SHEATH FLUID BYPASS CHANNEL
156: COMMUNICATION OPENING
162: COLLECTION OPENING
311: DISPLACEMENT PLATE
11: SAMPLE FLUID INLET
13: SHEATH FLUID INLET
15: MAIN CHANNEL
17: WASTE CHANNEL
31: ACTUATOR
161: PRESSURE CHAMBER
181: DISCHARGE OPENING
$a_1 \sim a_3$: SUBSTRATE LAYER

(56) References Cited

FOREIGN PATENT DOCUMENTS

JP      2009-100698 A      5/2009
JP      2012-127922 A      7/2012

OTHER PUBLICATIONS

Final Rejection for U.S. Appl. No. 13/963,188, dated Jan. 22, 2016, 08 pages.
Advisory Action (PTOL-303) for U.S. Appl. No. 13/963,188, dated Apr. 21, 2016, 03 pages.
Non-Final Rejection for U.S. Appl. No. 13/963,188, dated Sep. 9, 2016, 07 pages.
Notice of Allowance and Fees Due (PTOL-85) for U.S. Appl. No. 13/963,188, dated Apr. 21, 2017, 08 pages.

- 1a: MICROCHIP
- 11: SAMPLE FLUID INLET
- 12: SAMPLE FLUID CHANNEL
- 13: SHEATH FLUID INLET
- 14: SHEATH FLUID CHANNEL
- 15: MAIN CHANNEL
- 15a: DETECTION AREA
- 16: SORTING CHANNEL
- 17: WASTE CHANNEL
- 18: SHEATH FLUID BYPASS CHANNEL
- 19: SORTING CHANNEL END
- 161: PRESSURE CHAMBER

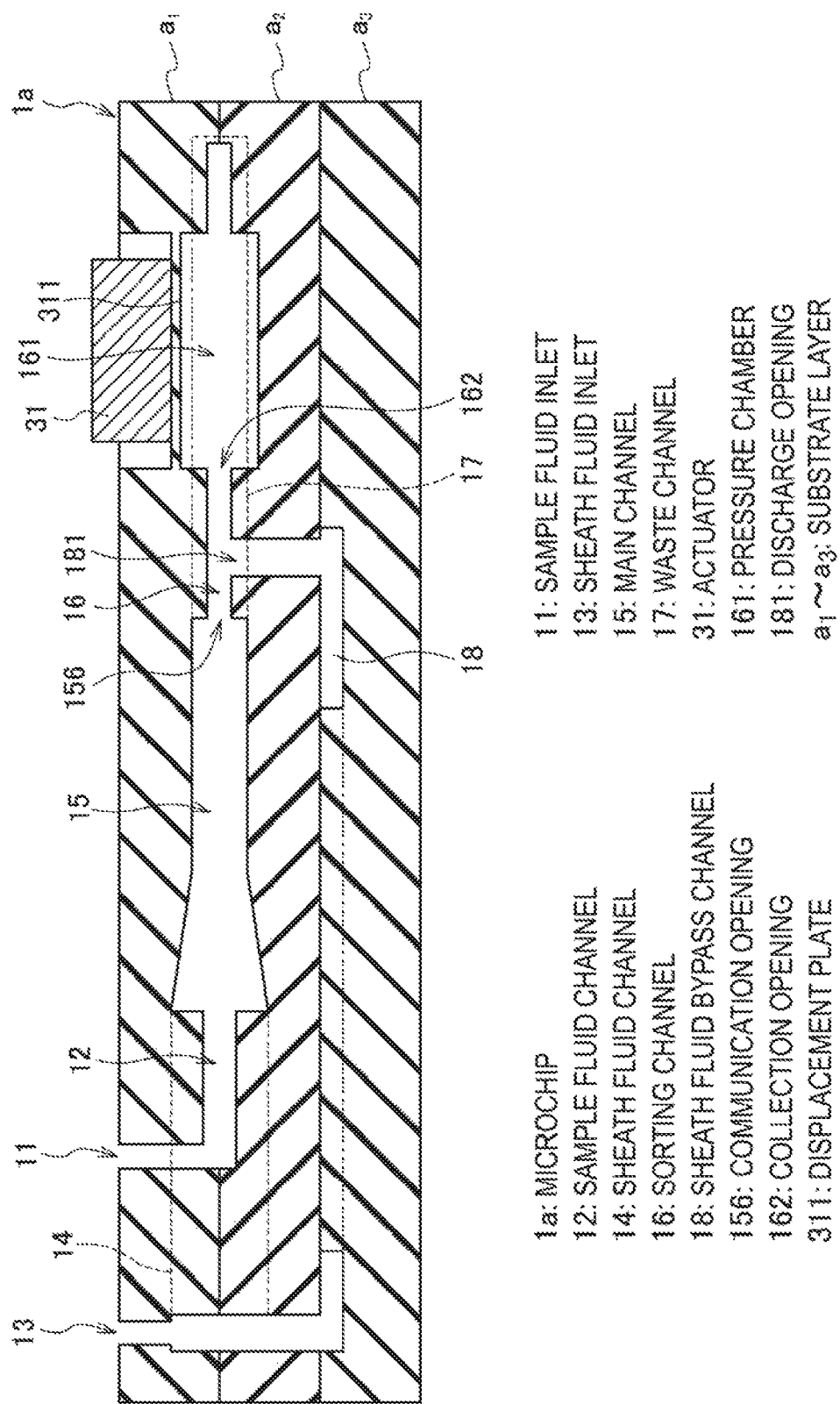

S: SAMPLE FLUID LAMINAR FLOW  
15: MAIN CHANNEL  
17: WASTE CHANNEL

T: SHEATH FLUID LAMINAR FLOW  
16: SORTING CHANNEL  
156: COMMUNICATION OPENING

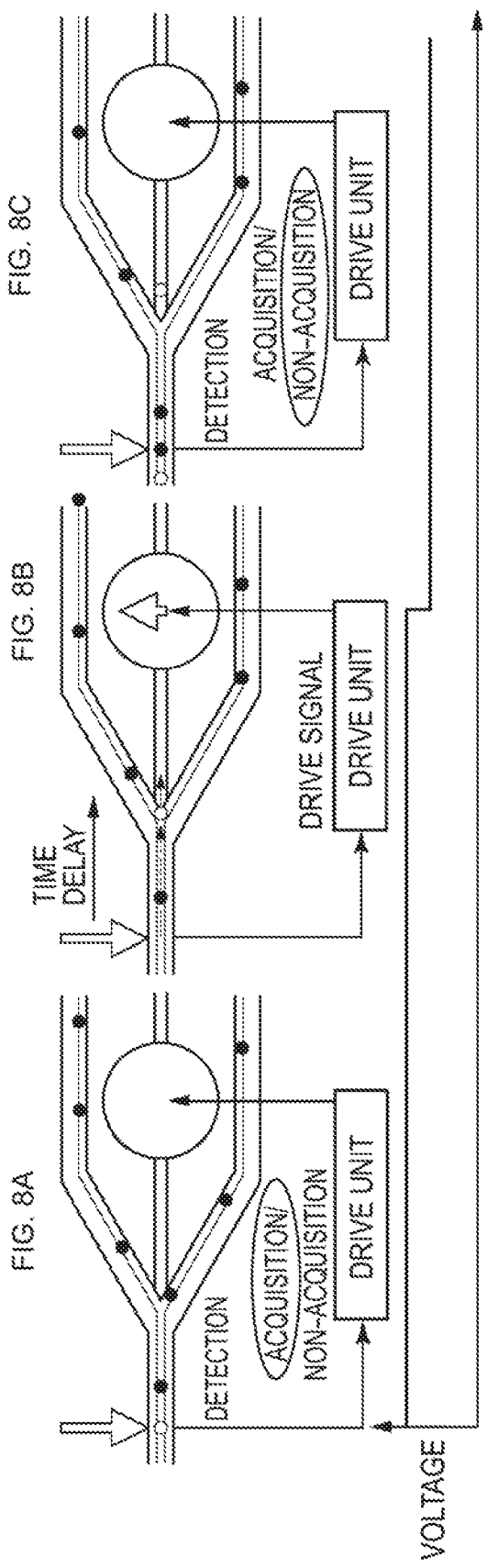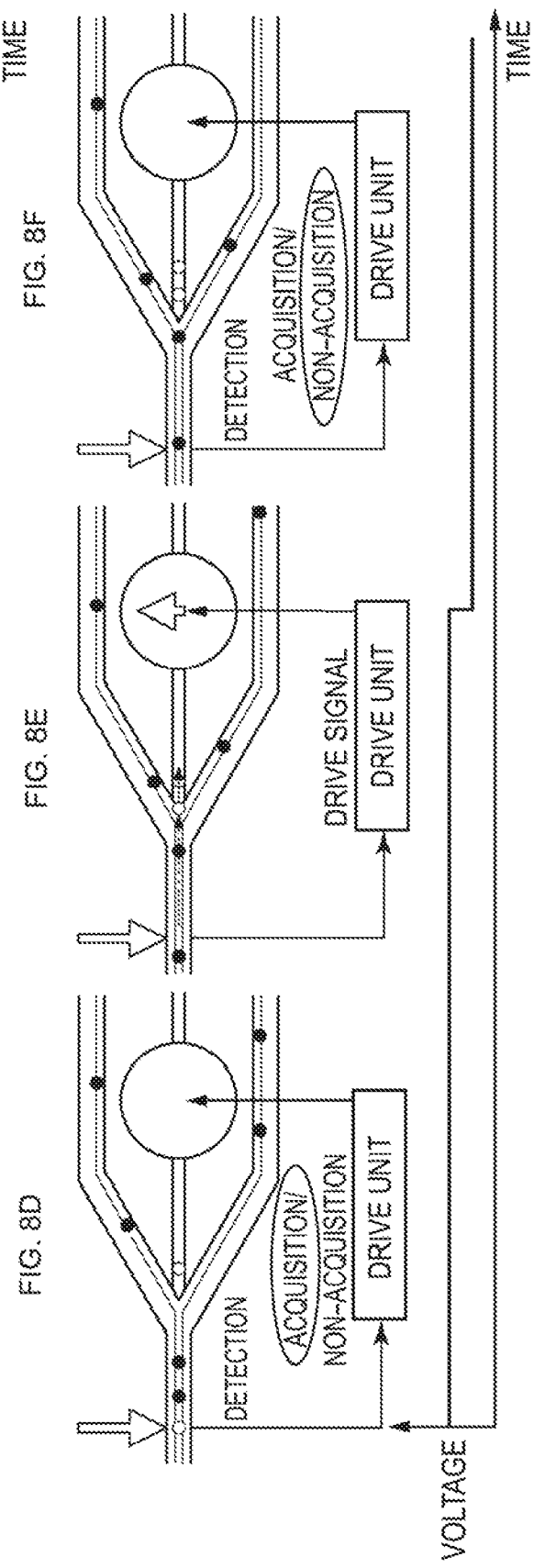

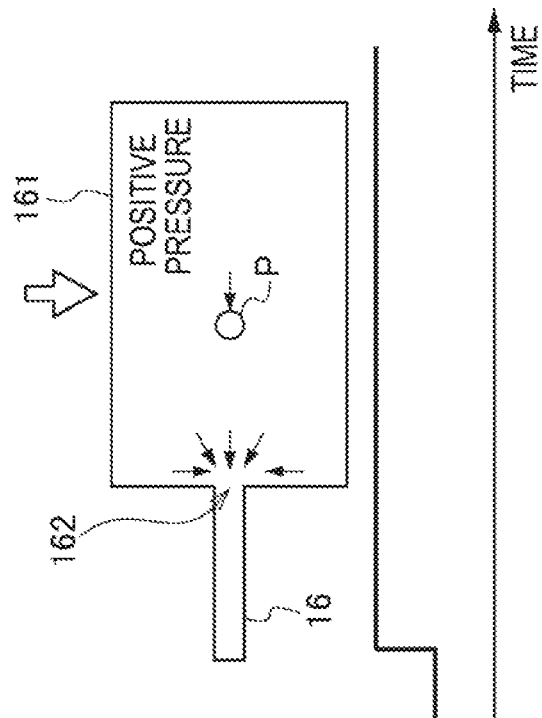
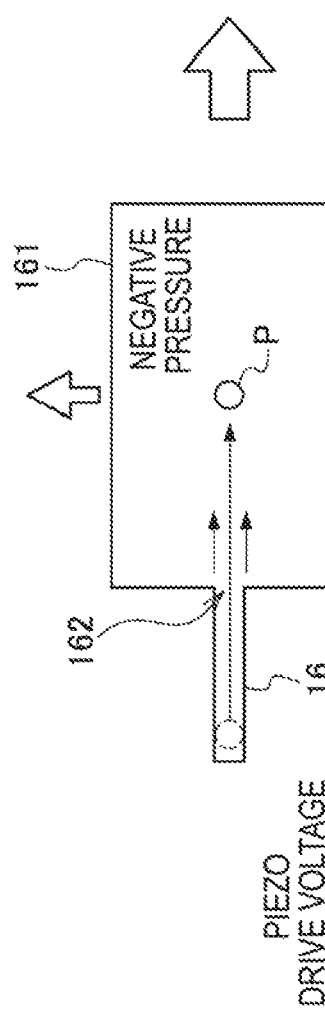

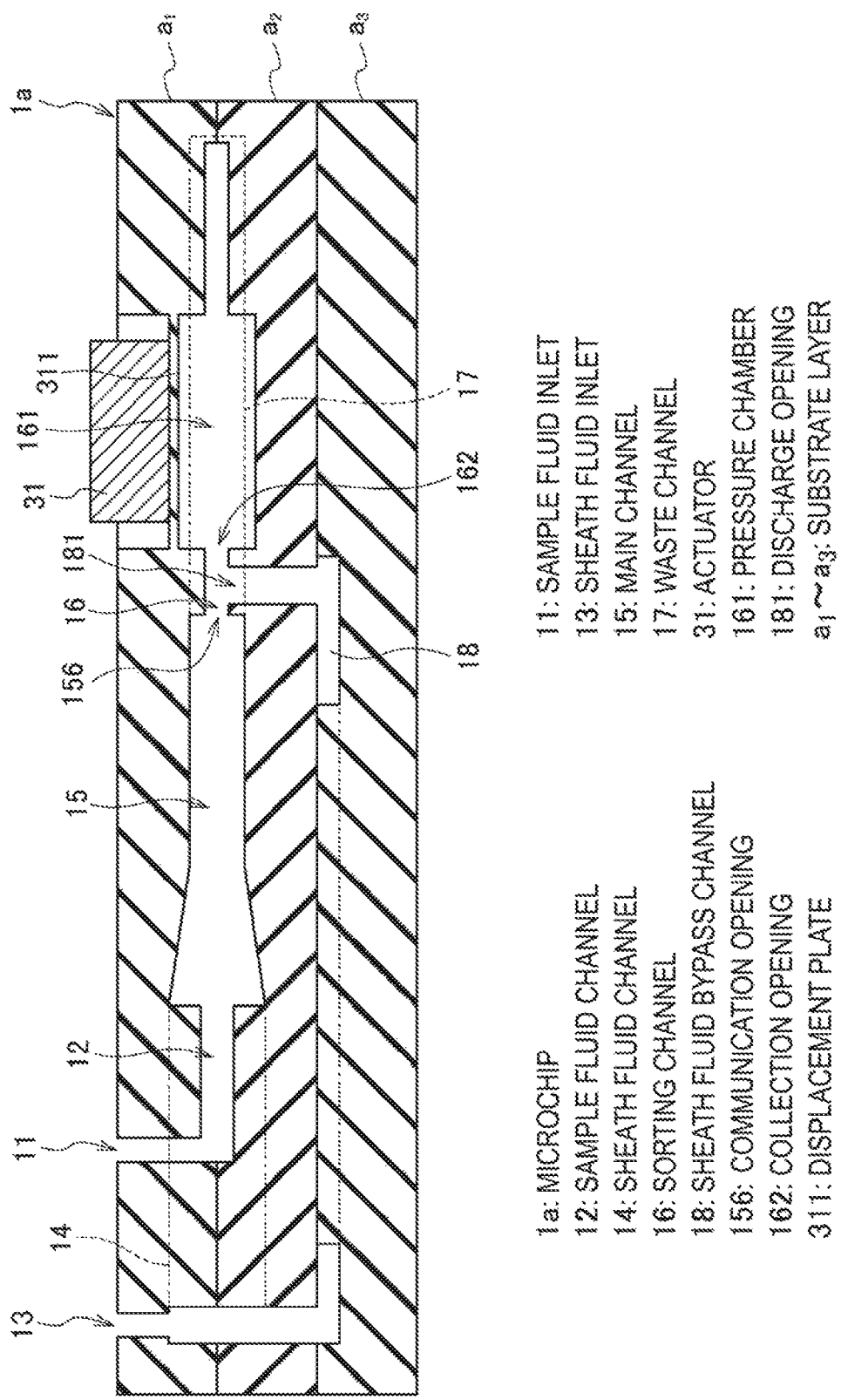

15: MAIN CHANNEL
17: WASTE CHANNEL
181: DISCHARGE OPENING

16: SORTING CHANNEL
18: SHEATH FLUID BYPASS CHANNEL
P: TARGET PARTICLE

PULSE WAVEFORM

STEP WAVEFORM

UNDERSHOOT-STEP WAVEFORM

MICROPARTICLE SORTING METHOD AND MICROCHIP FOR SORTING MICROPARTICLES

CROSS REFERENCE TO RELATED APPLICATION

The present application is a divisional application of U.S. patent application Ser. No. 13/963,188, filed Aug. 9, 2013, which claims the priority from prior Japanese Priority Patent Application JP 2012-180317 filed in the Japan Patent Office on Aug. 16, 2012, the entire content of which is hereby incorporated by reference.

BACKGROUND

The present technology relates to a microparticle sorting method. More specifically, the present technology relates to a microparticle sorting method that separates and recovers only target microparticles from the microparticles that are flowing along a channel.

A microparticle sorting apparatus that forms a microparticle-containing sheath flow in a channel, detects fluorescence and scattered light emitted from the microparticles by irradiating light on the microparticles in the sheath flow, and separates and recovers a microparticle group (population) that exhibits a predetermined optical characteristic is known. For example, in a flow cytometer, a specific type of cell only is separated and recovered by labeling a plurality of types of cell included in a sample with a fluorescent dye and optically identifying the fluorescent dye labeled on each cell.

In JP 2009-100698A and JP 2005-538727T, microchip-type microparticle sorting apparatuses are disclosed that perform analysis by forming a sheath flow in a channel formed on a microchip that is made from plastic, glass or the like.

The microparticle sorting apparatus disclosed in JP 2009-100698A controls the feeding direction of the sheath flow at a branching portion between an introduction channel in which the sheath flow is formed and a branch channel in communication with the introduction channel by generating an air bubble based on laser irradiation at the branching portion. According to this microparticle sorting apparatus, controlling the feeding direction of the sheath flow at the branching portion with an air bubble enables just the target microparticles to be collected into the branch channel from the introduction channel and sorted.

Further, the microfluidic system disclosed in JP 2005-538727T sorts target microparticles by using an actuator to control the feeding direction of a sheath flow at a channel branching portion. In this microfluidic system, the actuator changes the feeding direction of the sheath flow by pressing against a chamber that is connected to a branching portion between an introduction channel in which the sheath flow is formed and a branch channel in communication with the introduction channel to push out fluid in the chamber.

SUMMARY

For microchip-type microparticle sorting apparatuses, in order to further increase the speed and accuracy of analysis, there is a demand for a technology for rapidly and stably extracting only target microparticles from a sheath flow that is flowing through a channel.

According to an embodiment of the present technology, there is provided a microparticle sorting technology that can rapidly and stably extract only target microparticles from a sheath flow that is flowing through a channel.

According to an embodiment of the present technology, there is provided a microparticle sorting method including a procedure of collecting a microparticle in a fluid that flows through a main channel in a branch channel that is in communication with the main channel by generating a negative pressure in the branch channel. In the procedure, a flow of a fluid is formed that flows toward a side of the main channel from a side of the branch channel at a communication opening between the main channel and the branch channel. The flow may be formed by introducing the fluid into the branch channel from an introduction opening positioned near the communication opening in the branch channel. The fluid introduced from the introduction opening into the branch channel is split into a counter flow that flows toward the communication opening and a forward flow that flows in the opposite direction.

In this microparticle sorting method, by maintaining the flow of the fluid formed in the communication opening that flows toward the main channel side from the branch channel side before and after the above-described steps, the fluid in the main channel can be prevented from unnecessarily entering the branch channel during the period that a negative pressure is not being generated in the branch channel.

According to the microparticle sorting method of the present technology, in the procedure, a flow rate of the fluid that is sucked into the branch channel from the main channel due to negative pressure may be greater than a flow rate of the fluid introduced into the branch channel from the introduction opening and fed toward the communication opening. The microparticle in the main channel may be hereby collected from the communication opening to a position that is past the introduction opening of the branch channel.

According to the microparticle sorting method of the present technology, in the procedure, the negative pressure may be generated by an actuator applying a force that deforms an inner space of the branch channel to cause a volume of the inner space to increase A change in the negative pressure may have a pulse waveform, a step waveform, or an undershoot-step waveform.

According to an embodiment of the present technology, there is provided a microchip for sorting microparticles, including a sample fluid introduction opening into which a sample fluid including a microparticle is introduced, a sample fluid channel through which the sample fluid introduced from the sample fluid introduction opening flows, a sheath fluid introduction opening into which a sheath fluid is introduced, a first sheath fluid channel through which the sheath fluid introduced from the sheath fluid introduction opening flows, a main channel where the sample fluid channel and the first sheath fluid channel merge, a branch channel that is in communication with the main channel, and a second sheath fluid channel that connects the sheath fluid introduction opening and a sheath fluid discharge opening that is positioned near a communication opening to the main channel in the branch channel, and that feeds the sheath fluid introduced from the sheath fluid introduction opening into the branch channel from the sheath fluid discharge opening. According to the microchip for sorting microparticles of the present technology, the second sheath fluid channel may not be in communication with the sample fluid channel, the first sheath fluid channel, or the main channel. An actuator for applying a displacement on a contact surface may be arranged in contact with a position corresponding to the branch channel on a surface. A pressure chamber for producing a change in volume due to the displacement may be configured in the branch channel. The communication opening, the sheath fluid discharge opening, and the pressure chamber may be arranged in the branch channel in order of mention. The microchip for sorting microparticles may further include the two first sheath fluid channels. The sheath fluid introduction opening may be provided at a symmetrical center of the two first sheath fluid channels. An end on an opposite side to the communication opening of the branch channel may be an open end.

In an embodiment of the present technology, the term "microparticle" has a broad meaning that includes biologically-relevant microparticles such as cells, microbes, ribosomes and the like, as well as synthetic particles such as latex particles, gel particles, industrial particles and the like.

Examples of biologically-relevant microparticles include the chromosomes, liposomes, mitochondria, organelles (cell organelles) that form various cells. Examples of cells include animal cells (hematopoietic cells etc.) and plant cells. Examples of microbes include bacteria such as E. coli, viruses such as tobacco mosaic virus, fungi such as yeast and the like. Further example of biologically-relevant microparticles includes nucleic acids, proteins, complexes of these and the like. Examples of industrial particles include organic or inorganic polymer materials, metals and the like. Examples of organic polymer materials include polystyrene, styrene-divinyl benzene, poly methyl methacrylate and the like. Examples of inorganic polymer materials include glass, silica, magnetic materials and the like. Examples of metals include metal colloids, aluminum and the like. Although the shape of these microparticles is usually spherical, the microparticles may also have a non-spherical shape. Further, the size and mass of these microparticles is not especially limited.

According to the embodiments of the present technology described above, a microparticle sorting technology is provided that can rapidly and stably extract only target microparticles from a sheath flow that is flowing through a channel.

BRIEF DESCRIPTION OF THE DRAWINGS

FIG. 3 is a diagram illustrating a configuration of the microchip 1a;

FIG. 4 is a diagram illustrating a configuration of the microchip 1a;

FIGS. 5A, 5B and 5C are diagrams illustrating a configuration of a branching portion between a main channel 15 and a sorting channel 16 of the microchip 1a;

FIG. 6 is a diagram illustrating a configuration of a sheath fluid inlet 13 side end of a sheath fluid bypass channel 18 of the microchip 1a;

FIG. 7 is a diagram illustrating a configuration of a discharge opening 181 side end of the sheath fluid bypass channel 18 of the microchip 1a;

FIGS. 8A, 8B, 8C, 8D, 8E and 8F are diagrams illustrating a sorting operation in the microparticle sorting apparatus A;

FIGS. 9A and 9B are diagrams illustrating functions of a pressure chamber 161 in the microchip 1a;

FIG. 10 is a diagram illustrating a configuration of a modified example of the microchip 1a;

FIG. 15 is a diagram illustrating a configuration of a modified example of the microchip 1a.

DETAILED DESCRIPTION OF THE EMBODIMENT(S)

Figure 1:
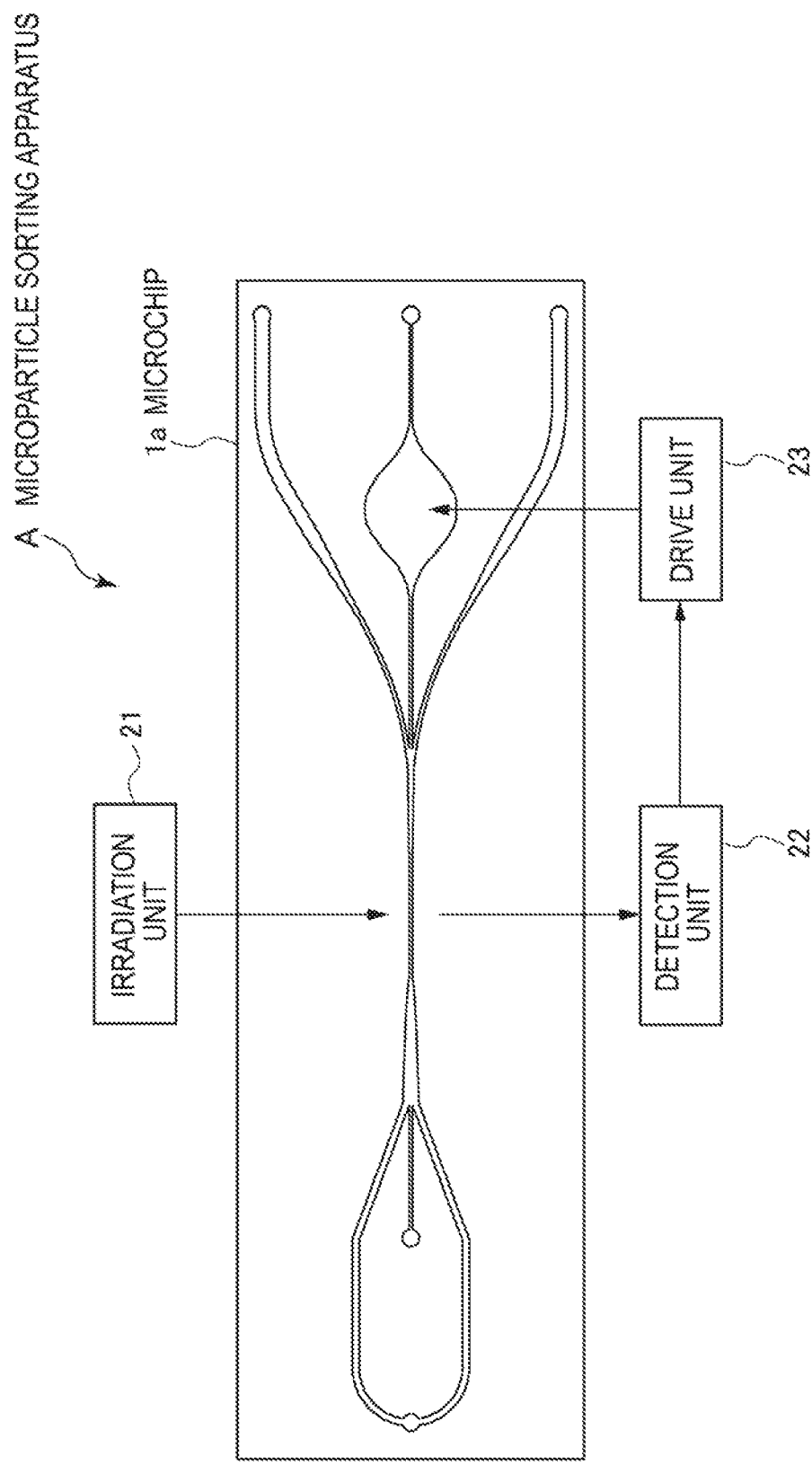
FIG. 1 is a diagram illustrating a configuration of a microparticle sorting apparatus A according to a first embodiment of the present technology.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. The description will be made in the following order.

1. Microparticle sorting apparatus and microchip for microparticle sorting that are capable of implementing the microparticle sorting method according to an embodiment of the present technology
(Overall configuration of the apparatus)
(Microchip configuration)
2. Microparticle sorting method according to an embodiment of the present technology
(Sorting operation)
(Counter Flow)
(Drive signal)
3. Modified example of the microparticle sorting method according to an embodiment of the present technology
4. Microparticle sorting program 1. Microparticle Sorting Apparatus and Microchip for Microparticle Sorting that are Capable of Implementing the Microparticle Sorting Method According to an Embodiment of the Present Technology
(Overall Configuration of the Apparatus)

Figure 2:
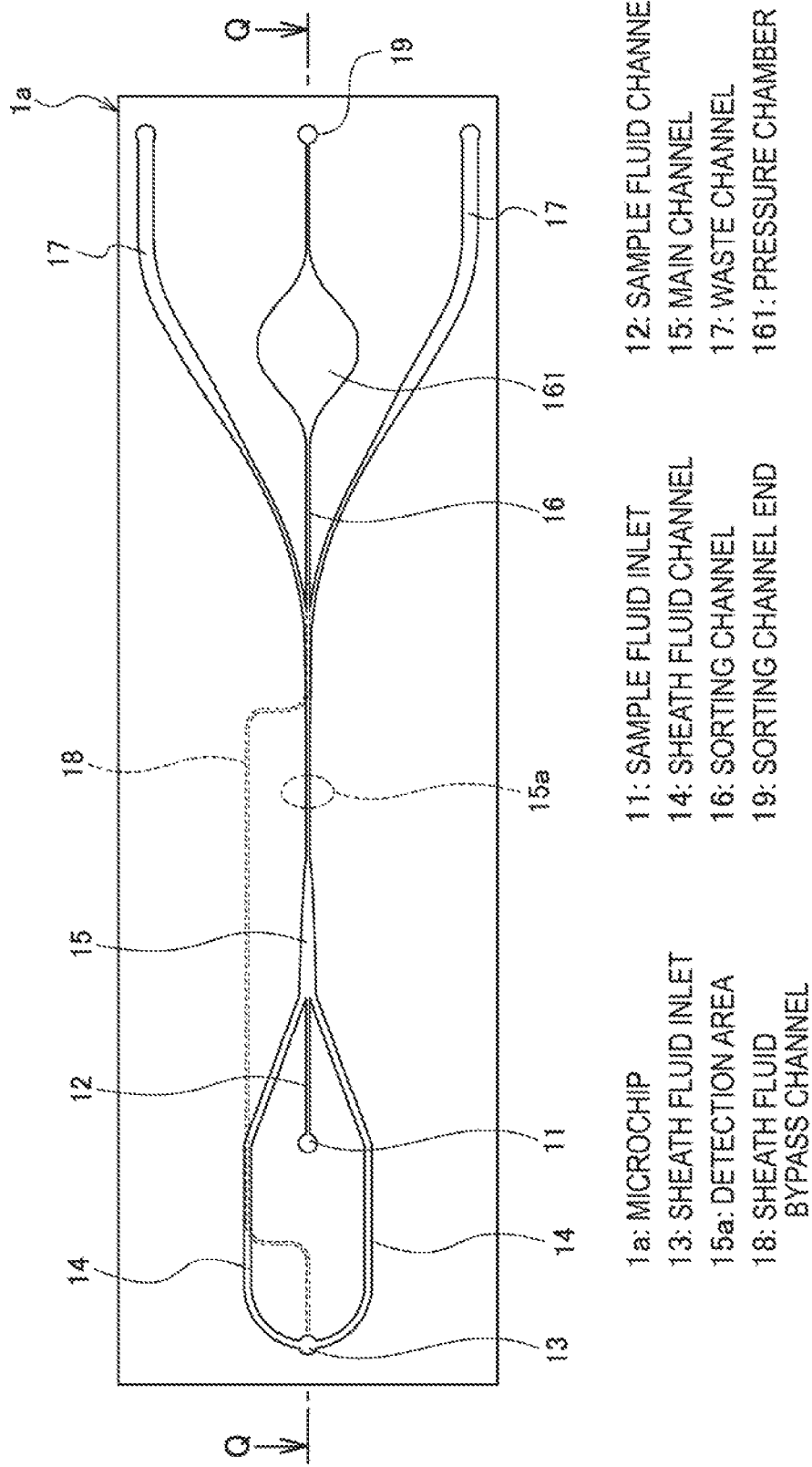
FIG. 2 is a diagram illustrating a configuration of a microchip 1a that is mounted on a microparticle sorting apparatus A.
Figure 3:
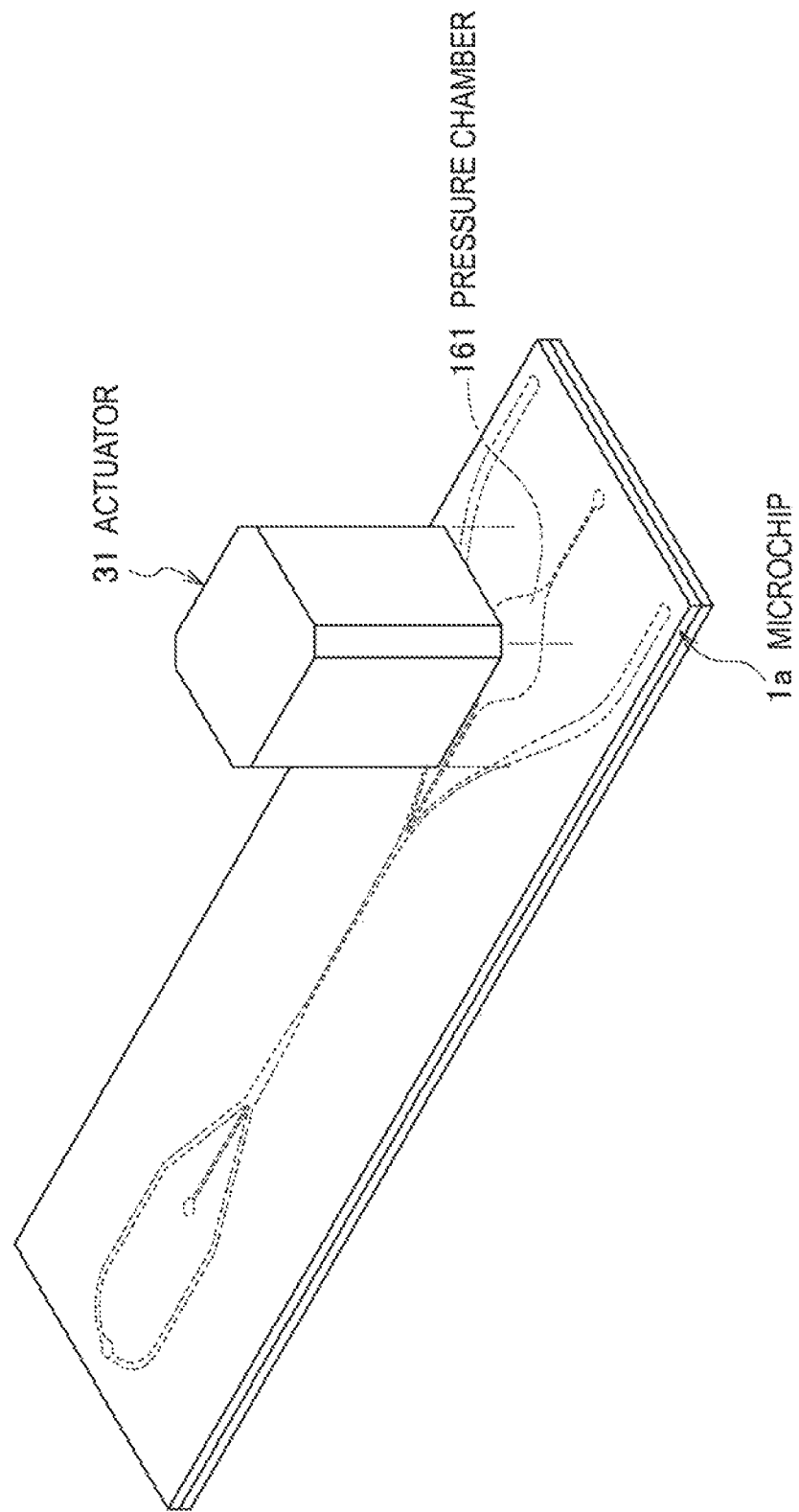

FIG. 1 is a diagram illustrating a configuration of a microparticle sorting apparatus A that is suited to implementing the microparticle sorting method according to an embodiment of the present technology. Further, FIGS. 2 to 4 are diagrams illustrating a configuration of a microchip 1a that is mounted on the microparticle sorting apparatus A. FIG. 2 is a top view, FIG. 3 is a perspective view, and FIG. 4 is a cross-sectional view along the cross-section Q-Q in FIG. 2.

The microparticle sorting apparatus A includes a microchip 1a, an irradiation unit 21, a detection unit 22, and a drive unit 23. On the microchip 1a is formed a main channel 15 through which a fluid (sample fluid) including microparticles that are the target of analysis (refer to FIG. 2). Further, an actuator 31 is arranged on the surface of the microchip 1a (refer to FIG. 3).

The irradiation unit 21 irradiates light (excitation light) on the microparticles flowing through the main channel 15 on the microchip 1a. The irradiation unit 21 includes, for example, a light source that emits excitation light and an objective lens that focuses the excitation light on the microparticles flowing through the main channel 15. The light source may be appropriately selected based on the analysis objective from among a laser diode, a SHG laser, a solid laser, a gas laser, a high luminance LED and the like. The irradiation unit 21 can optionally also have optical elements other than the light source and the objective lens.

The detection unit 22 detects fluorescence and scattered light that are emitted from the microparticles due to the irradiation with excitation light. The detection unit 22 includes an objective lens, which focuses the fluorescence and scattered light emitted from the microparticles, a detector and the like. The detection unit 22 may optionally also have optical elements other than the objective lens and the detector.

The fluorescence that is detected by the detection unit 22 may be fluorescence emitted from the microparticles themselves or fluorescence emitted from a fluorescent substance that is labeled on the microparticles. Further, the scattered light that is detected by the detection unit 22 may be various types of scattered light, such as forward scattered light, side scattered light, Rayleigh scattered light, and Mie scattering.

The fluorescence and scattered light detected by the detection unit 22 are converted into an electric signal, and the electric signal is output to the drive unit 23. The drive unit 23 determines the optical characteristics of the microparticles based on the input electric signal. Further, the drive unit 23 has a function for collecting microparticles that have been determined to satisfy a predetermined characteristic from the main channel 15 in a sorting channel 16 by applying a voltage to the actuator 31 and controlling that voltage. This function of the drive unit 23 will be described in more detail below. The drive unit 23 is configured from a hard disk in which programs and an OS for executing the below-described various processes are stored, a CPU, a memory and the like.

(Microchip Configuration)

The configuration of the microchip 1*a* will now be described in more detail with reference to FIGS. 2 to 4. A sample fluid that includes microparticles is introduced from a sample fluid inlet 11 into a sample fluid channel 12. Further, a sheath fluid is introduced from a sheath fluid inlet 13. The sheath fluid introduced from the sheath fluid inlet 13 is split and fed into two sheath fluid channels 14 and 14. The sample fluid channel 12 and the sheath fluid channels 14 and 14 merge to form the main channel 15. A sample fluid laminar flow fed through the sample fluid channel 12 and a sheath fluid laminar flow fed through the sheath fluid channels 14 and 14 merge in the main channel 15, and form a sheath flow in which the sample fluid laminar flow is sandwiched by the sheath fluid laminar flow.

Further, the sheath fluid introduced from the sheath fluid inlet 13 is also fed to a sheath fluid bypass channel 18 that is formed separately to the sheath channel 14. One end of the sheath fluid bypass channel 18 is connected to the sheath fluid inlet 13, and the other end is connected in the vicinity of the communication opening to the main channel 15 of a below-described sorting channel 16 (refer to FIG. 4). Although the sheath fluid introduction end of the sheath fluid bypass channel 18 may be connected to any site where the sheath fluid is flowing, including the sheath fluid inlet 13 and the sheath fluid channels 14 and 14, it is preferred that the sheath fluid bypass channel 18 is connected to the sheath fluid inlet 13. By connecting the sheath fluid bypass channel 18 at a center position (i.e., in the present embodiment, at the sheath fluid inlet 13) where the two sheath fluid channels 14 are geometrically symmetrical, equal amounts of the sheath fluid flow can be made to flow to the two sheath fluid channels 14. Reference numeral 156 in FIG. 4 denotes a communication opening of the sorting channel 16 to the main channel 15, and reference numeral 181 denotes a discharge opening to the sorting channel 16 of the sheath fluid that is fed through the sheath fluid bypass channel 18.

Reference numeral 15*a* in FIG. 2 denotes a detection area where excitation light is irradiated by the irradiation unit 21 and fluorescence and scattered light are detected by the detection unit 22. The microparticles are fed to the detection area 15*a* in a single line arranged in the sheath flow formed in the main channel 15, and are irradiated with the excitation light from the irradiation unit 21.

Figure 5A:
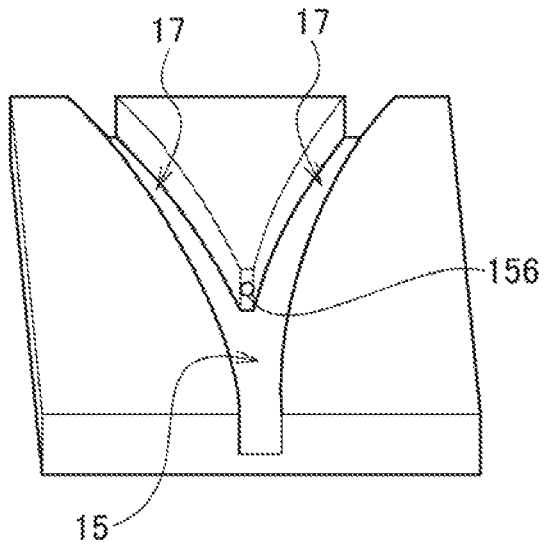
Figure 5B:
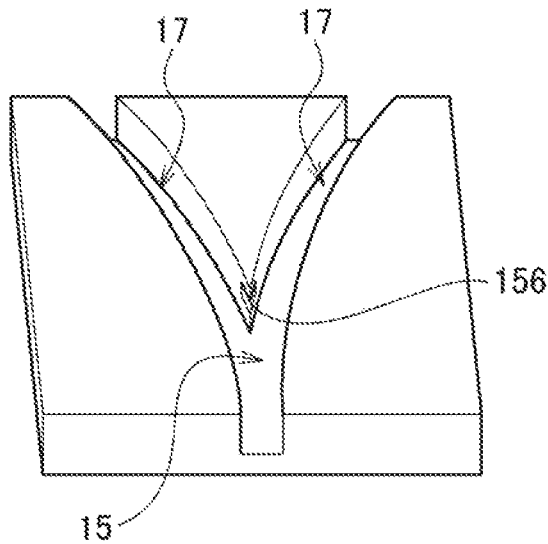
Figure 5C:
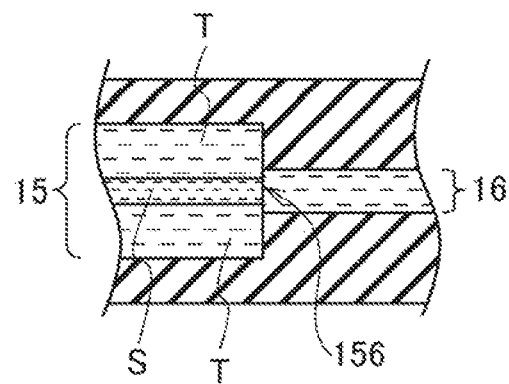

The main channel 15 splits into three channels downstream from of the detection area 15*a*. A configuration of the branching portion of the main channel 15 is illustrated in FIGS. 5A, 5B and 5C. Downstream from the detection area 15*a*, the main channel 15 is in communication with three branch channels, the sorting channel 16 and waste channels 17 and 17. Of these, the sorting channel 16 is a channel into which microparticles that have been determined by the drive unit 23 to satisfy a predetermined optical characteristic (hereinafter referred to as "target particles") are collected. On the other hand, microparticles that are determined by the drive unit 23 as not satisfying the predetermined optical characteristic (hereinafter referred to as "non-target particles") are not collected in the sorting channel 16, and flow into either of the two waste channels 17 and 17.

The sheath fluid bypass channel 18 is connected to the discharge opening 181 positioned near the communication opening 156 to the main channel 15 of the sorting channel 16 (refer to FIG. 4). The sheath fluid introduced from the sheath fluid inlet 13 is introduced from the discharge opening 181 into the sorting channel 16, and forms a sheath fluid flow at the communication opening 156 that flows from the sorting channel 16 side toward the main channel 15 side (this flow will be described in more detail blow).

Figure 6:
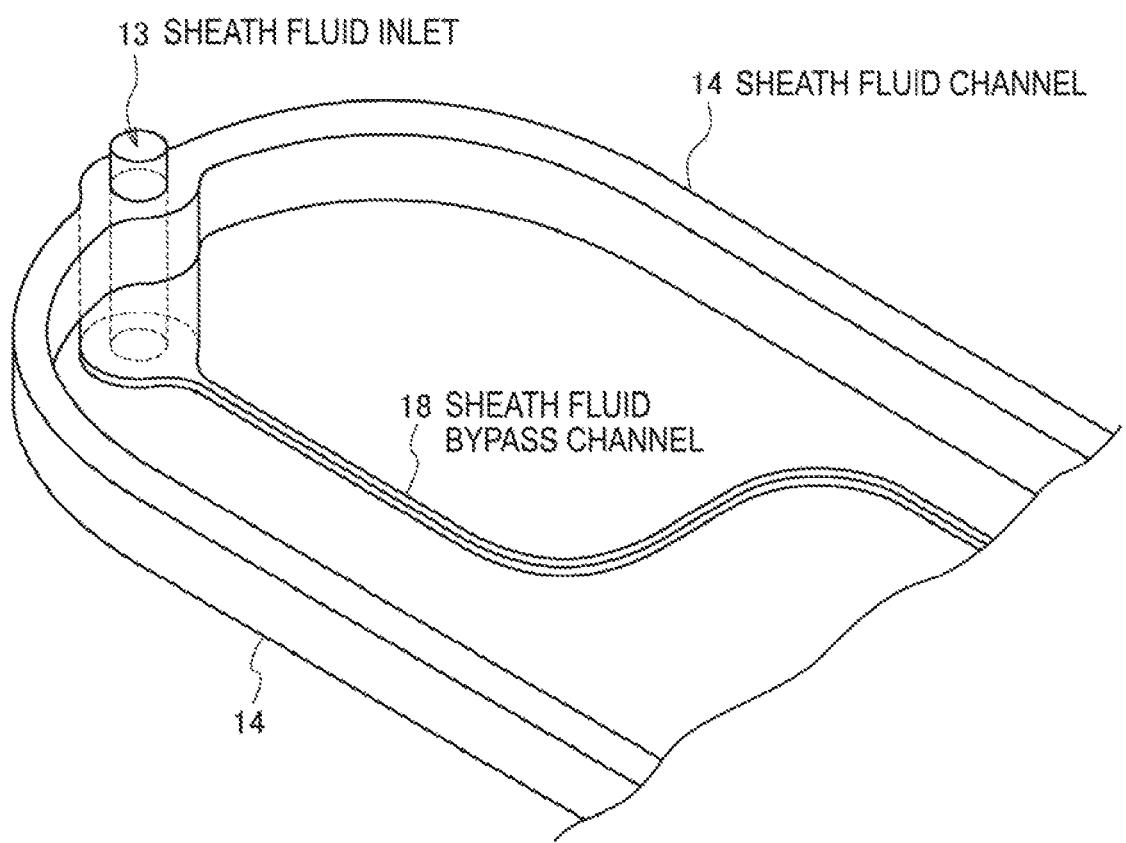
Figure 7:
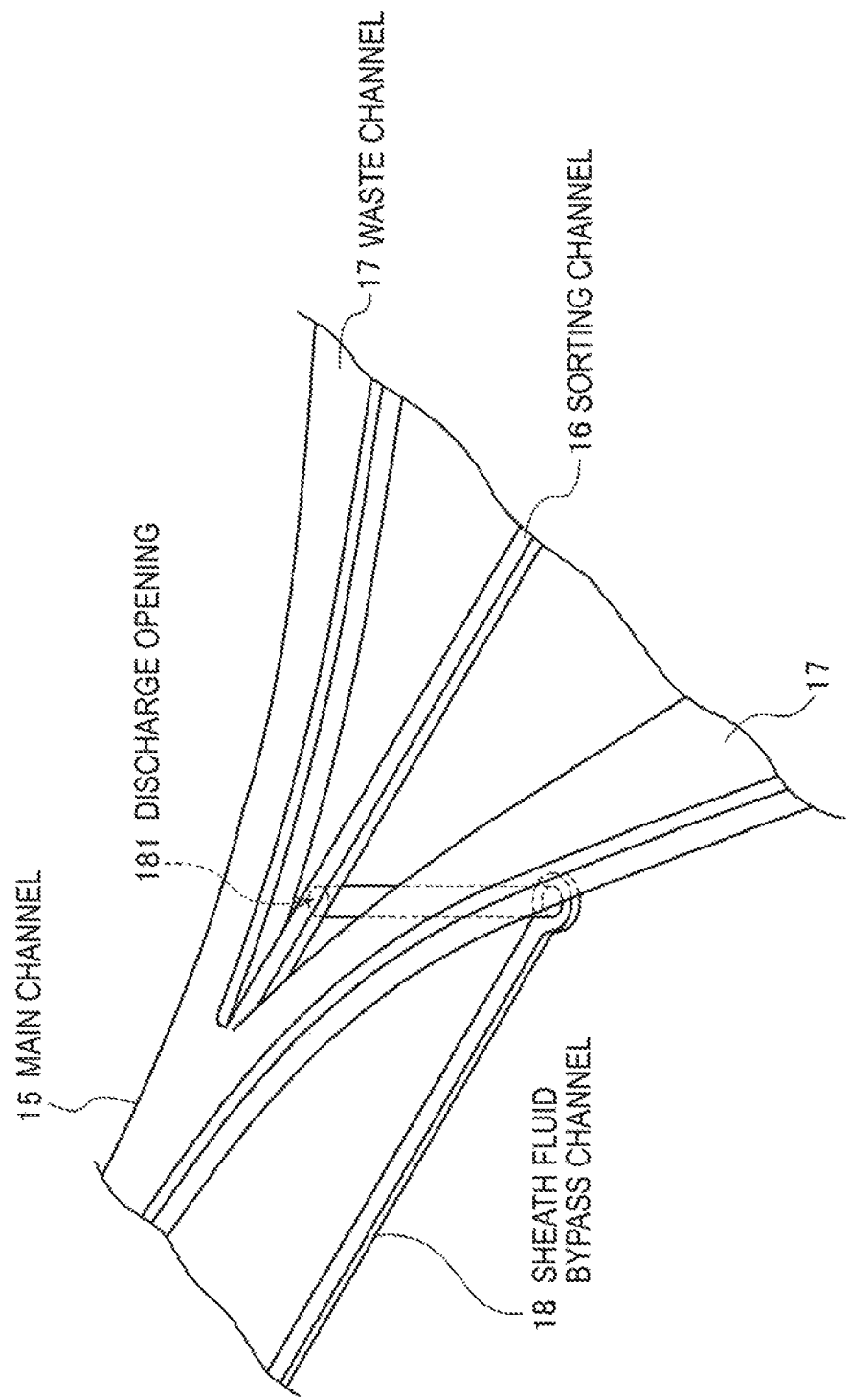

The microchip 1*a* is formed from three substrate layers. The sample fluid channel 12, the sheath flow channel 14, the main channel 15, the sorting channel 16, and the waste channel 17 are formed by a first substrate layer a1 and a second substrate layer a2 (refer to FIG. 4). On the other hand, the sheath fluid bypass channel 18 is formed by the second substrate layer a2 and a third substrate layer a3. The sheath fluid bypass channel 18 formed by the substrate layers a2 and a3 is connected with the sheath fluid inlet 13 and the discharge opening 181 of the sorting channel 16 without being in communication with the sample fluid channel 12, the sheath channel 14, or the main channel 15. The configuration of the sheath fluid inlet 13 side end and of the discharge opening 181 side end of the sheath fluid bypass channel 18 is illustrated in FIGS. 6 and 7, respectively.

It is noted that the layer configuration of the substrate layers of the microchip 1*a* is not limited to three layers. Further, the configuration of the sheath fluid bypass channel 18 is also not limited to that illustrated in the drawings, as long as the sheath fluid bypass channel 18 is connected with the sheath fluid inlet 13 and the discharge opening 181 of the sorting channel 16 without meeting the sample fluid channel 12, the sheath channel 14, or the main channel 15.

The collecting of the target particles into the sorting channel 16 is performed by generating a negative pressure in the sorting channel 16 with the actuator 31 to suck the sample fluid including the target particles and the sheath fluid into the sorting channel 16. The actuator 31 is a piezo element or similar device. The actuator 31 is arranged in contact with the surface of the microchip 1*a*, at a position corresponding to the sorting channel 16. More specifically, the actuator 31 is arranged at a position corresponding to a pressure chamber 161 that is provided in the sorting channel 16 as an area whose inner space has expanded (refer to FIGS. 3 and 4). The pressure chamber 161 is positioned downstream from of the communication opening 156 and the discharge opening 181 in the sorting channel 16.

The inner space of the pressure chamber 161 is, as illustrated in FIG. 2, expanded in a planar direction (width direction of the sorting channel 16), and as illustrated in FIG. 4, expanded in a cross-sectional direction (height direction of the sorting channel 16). Namely, the sorting channel 16 is expanded in the width direction and in the height direction at the pressure chamber 161. In other words, the sorting channel 16 is formed so that its vertical cross-section increases in size in the flow direction of the sample fluid and the sheath fluid at the pressure chamber 161.

The actuator 31 causes the pressure in the sorting channel 16 to change via the surface (contact face) of the microchip 1a by producing a stretching force due to a change in the applied voltage. When a flow is produced in the sorting channel 16 due to a change in the pressure in the sorting channel 16, the volume of the sorting channel 16 simultaneously changes too. The volume of the sorting channel 16 changes until it reaches a volume that is stipulated based on the displacement of the actuator 31 corresponding to the applied voltage. More specifically, when a voltage has been applied and the sorting channel 16 is in a stretched state, the actuator 31 keeps the volume of the pressure chamber 161 small by pressing against a displacement plate 311 forming the pressure chamber 161 (refer to FIG. 4). When the applied voltage decreases, the actuator 31 generates a force in a contracting direction, whereby the pressing against the displacement plate 311 weakens and a negative pressure is generated in the pressure chamber 161.

In order to efficiently transmit the stretching force of the actuator 31 into the pressure chamber 161, as illustrated in FIG. 4, it is preferred to form a recess on the surface of the microchip 1a at the position corresponding to the pressure chamber 161, and arrange the actuator 31 in this recessed portion. Consequently, the displacement plate 311 that serves as the contact face of the actuator 31 can be made thinner, so that the displacement plate 311 can be easily displaced by changes in the pressing force generated by expansion and contraction of the actuator 31, allowing the volume of the pressure chamber 161 to change.

In FIGS. 4, 5A, 5B and 5C, reference numeral 156 denotes a communication opening of the sorting channel 16 to the main channel 15. The target particles being fed in the sheath flow formed in the main channel 15 are collected in the sorting channel 16 from the communication opening 156. To facilitate the collection of the target particles in the sorting channel 16 from the main channel 15, as illustrated in FIG. 5C, it is desirable to form the communication opening 156 so as to open onto a position corresponding to a sample fluid laminar flow S in the sheath flow formed in the main channel 15. The shape of the communication opening 156 is not especially limited, and may be, for example, a flat opening shape like that illustrated in FIG. 5A, or a notched opening shape like that illustrated in FIG. 5B formed by cutting the channel walls of the two waste channels 17.

The microchip 1a can be configured by laminating a substrate layer on which the main channel 15 and the like are formed. The formation of the main channel 15 and the like on the substrate layer can be carried out by injection molding of a thermoplastic resin using a mold. Examples of thermoplastic resins that can be used include plastics that are known as related-art microchip materials, such as polycarbonate, polymethyl methacrylate resin (PMMA), cyclic polyolefins, polyethylene, polystyrene, polypropylene, and polydimethylsiloxane, (PDMS).

2. Microparticle Sorting Method According to an Embodiment of the Present Technology (Sorting Operation)

Next, the operation of the microparticle sorting apparatus A will be described.

When the user starts analysis, the microparticle sorting apparatus A drives a pump to feed the sample fluid and the sheath fluid to the sample fluid inlet 11 and the sheath fluid inlet 13 of the microchip 1a. Consequently, a sheath flow in which the sample fluid laminar flow is sandwiched by the sheath fluid laminar flow is formed in the main channel 15.

The microparticles are fed to the detection area 15a in a single line arranged in the sheath flow, and are irradiated by the excitation light from the irradiation unit 21. Fluorescence and scattered light emitted from the microparticles due to the irradiation of excitation light are detected by the detection unit 22, and converted into an electric signal. The electric signal is output to the drive unit 23.

The drive unit 23 determines the optical characteristics of the microparticles based on the input electric signal. If a microparticle is determined to be a target particle, as illustrated in FIGS. 8A and 8B, after the time (delay period) that the target particle takes to move from the detection area 15a to the branching portion has elapsed, the drive unit 23 issues a drive signal to the actuator 31 for acquiring this microparticle. At this point, if necessary, the drive unit 23 can also be configured to drive the actuator 31 via an amplifier.

Specifically, if the actuator 31 is a piezo element, the drive unit 23 produces a negative pressure in the sorting channel 16 by applying a voltage that causes piezo contraction, which causes the volume of the pressure chamber 161 to increase, whereby the target particles collect in the sorting channel 16 from the main channel 15.

On the other hand, if it is determined that a microparticle is not a target particle, as illustrated in FIGS. 8C and 8D, the drive unit 23 issues a non-acquisition drive signal to the actuator 31, and performs optical characteristics determination of the next microparticle. It is noted that if the actuator 31 has received a non-acquisition drive signal, the actuator 31 does not operate.

The drive unit 23 repeats the optical characteristics determination of the microparticles and the output of a drive signal to the actuator 31 until analysis is finished (refer to FIGS. 8E and 8F), so that only the target particles accumulate in the sorting channel 16 (refer to FIG. 8F). After analysis has finished, the target particles that have been separated into the sorting channel 16 are recovered by the user.

As illustrated in FIG. 9A, the target particles drawn into the sorting channel 16 are collected in the pressure chamber 161. In the drawing, reference symbol P represents a target particle that has been collected in the pressure chamber 161, and reference numeral 162 denotes a collection opening for the target particle P into the pressure chamber 161. The flow of the sample fluid including the target particle P and the sheath fluid turns into a jet when flowing into the pressure chamber 161, whose interior air has been expanded, and breaks away from the channel wall face (refer to the arrow in FIG. 9A). Consequently, the target particle P separates from the collection opening 162, and is collected at the back of the pressure chamber 161.

Since the target particles are drawn from the main channel 15 into the pressure chamber 161, the amount of expansion in the volume of the pressure chamber 161 is preferably greater than the volume of the sorting channel 16 from the communication opening 156 until the collection opening 162 (refer to FIG. 4). Further, the amount of expansion in the volume of the pressure chamber 161 is preferably set to be an amount that generates a negative pressure that is sufficient to cause the flow of the sample fluid including the target particle P and the sheath fluid to break away from the channel wall face at the collection opening 162. The drive unit 23 outputs to the actuator 31 a piezo contraction signal with a voltage width that corresponds to this amount of increase in volume.

Like in the modified example illustrated in FIG. 10, the length of the sorting channel 16 from the communication opening 156 to the collection opening 162 may be designed to be shorter. The shorter the length from the communication opening 156 to the collection opening 162 is, the smaller the volume of the sorting channel 16 from the communication opening 156 to the collection opening 16 is. This means that the amount of increase in the volume of the pressure chamber 161 for drawing the target particles from the main channel 15 into the pressure chamber 161 is smaller. Consequently, the width of the voltage applied on the actuator 31 can be decreased, thereby enabling an efficient sorting operation.

Thus, by collecting the target particle P at the back of the pressure chamber 161 whose inner space has been expanded in the sorting channel 16, the target particle P can be prevented from flowing back out from the pressure chamber 161 toward the main channel 15 side even when the pressure in the sorting channel 16 reverses and becomes positive. As illustrated in FIG. 9B, even when the pressure in the sorting channel 16 is positive, since the sample fluid and the sheath fluid flow out over a wide area from the vicinity of the collection opening 162, the movement amount of the target particle P itself that has been collected at a position away from the collection opening 162 is small. Consequently, the target particle P does not flow back out, and is held in the pressure chamber 161.

(Counter Flow)

Figure 11:
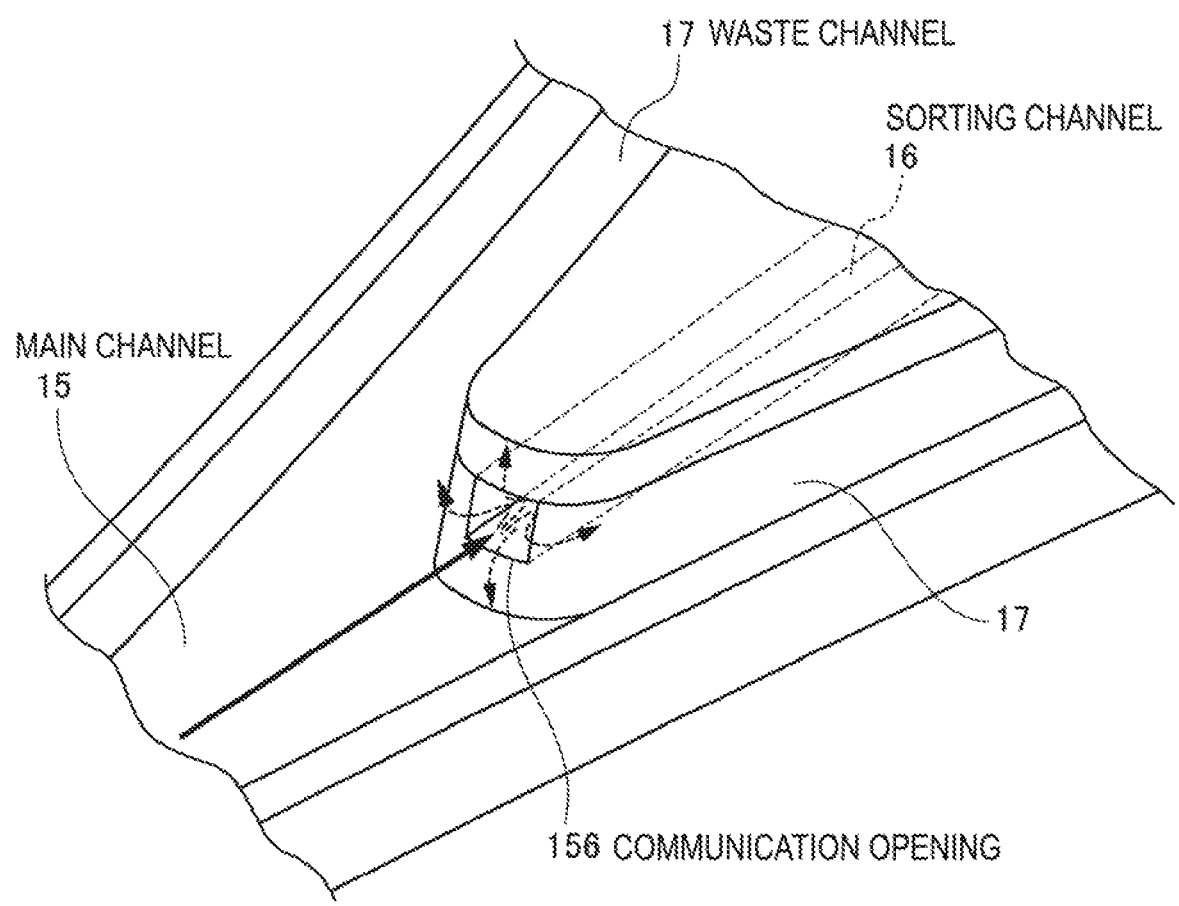
FIG. 11 is a diagram illustrating a flow of a sample fluid and a sheath fluid that may be produced at a branching portion between the main channel 15 and the sorting channel 16.

When the drive unit 23 determines that a microparticle is a non-target particle (when a sorting operation is not being performed), it is preferred that the non-target particle, or a sample fluid containing the non-target particle, and the sheath fluid do not enter the sorting channel 16. However, as illustrated in FIG. 11, since the flow of the sample fluid and the sheath fluid fed through the main channel 15 (refer to the solid-line arrow in the drawing) has a large momentum, the flow of the sample fluid and the sheath fluid that has flowed from the communication opening 156 into the sorting channel 16 changes direction in the sorting channel 16, and flows along the channel wall of the sorting channel 16 and out the main channel 15 side (refer to the dotted-line arrow in the drawing).

The flow of the sample fluid and the sheath fluid that has flowed along the channel wall from the sorting channel 16 and out the main channel 15 side is slow due to being constricted by the channel wall, so that an accumulation of the non-target particles, or a sample fluid containing non-target particles, and the sheath fluid is produced at the communication opening 156. This accumulation hinders the sorting operation of the target particles and the non-target particles from being carried out quickly.

Figure 12A:
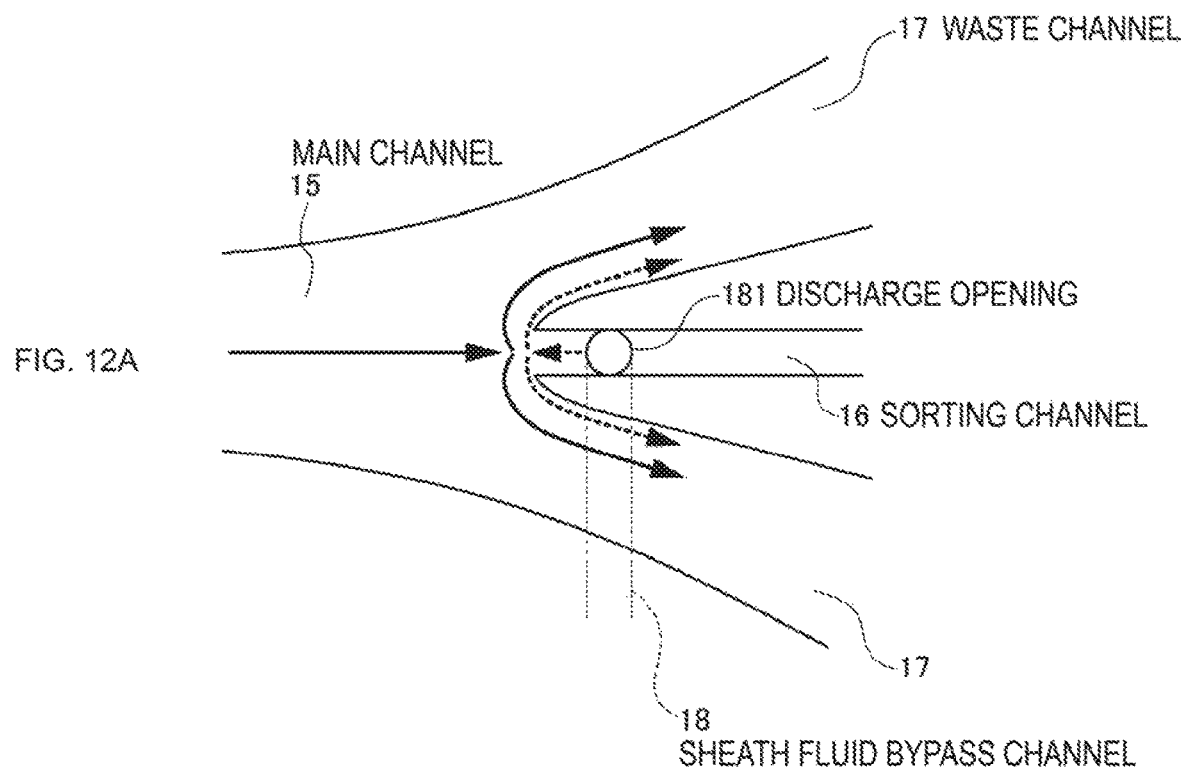
FIGS. 12A and 12B are diagrams illustrating a flow of the sheath fluid introduced from the discharge opening 181 of the sorting channel 16.

In the microparticle sorting apparatus A, the sheath fluid introduced into the sorting channel 16 from the discharge opening 181 by the sheath fluid bypass channel 18 acts to suppress the non-target particles, or a sample fluid containing non-target particles, and the sheath fluid from entering the sorting channel 16 when a sorting operation is not being performed. Namely, the sheath fluid introduced from the sheath fluid inlet 13 is introduced into the sorting channel 16 from the discharge opening 181, and forms a sheath fluid flow (hereinafter, "counter flow") at the communication opening 156 that flows from the sorting channel 16 side to the main channel 15 side (refer to FIG. 12A). Further, this counter flow opposes the flow of the sample fluid and the sheath fluid that is trying to enter the sorting channel 16 from the main channel 15, thereby inhibiting entry of the sample fluid and the sheath fluid into the sorting channel 16.

It is preferred that the counter flow has a momentum that matches the momentum (force) of the flow of the sample fluid and the sheath fluid that is trying to enter the sorting channel 16 from the main channel 15. The momentum of the counter flow can be controlled by adjusting the amount of sheath fluid that is fed to the sheath fluid bypass channel 18. This fed amount can be controlled by adjusting the channel diameter of the sheath fluid bypass channel 18. Further, the adjustment of the fed amount can also be carried out using a feed unit such as a syringe pump or a valve provided in the sheath fluid bypass channel 18.

The flow rate ratio of the flow rate of the sheath fluid introduced from the sheath fluid inlet 13 to the sheath channel 14 to the flow rate to the sheath fluid bypass channel 18 is determined based on the flow resistance ratio of both channels. Consequently, even if the introduction pressure of the sheath fluid to the sheath fluid inlet 13 varies, a stable operation can be carried out without this flow rate ratio fluctuating. Further, even if the sheath fluid flow rate is changed in order to change the flow velocity of the microparticles at the detection area 15a, the flow rate to the sheath channel 14 and the flow rate to the sheath fluid bypass channel 18 may be individually controlled.

Figure 12B:
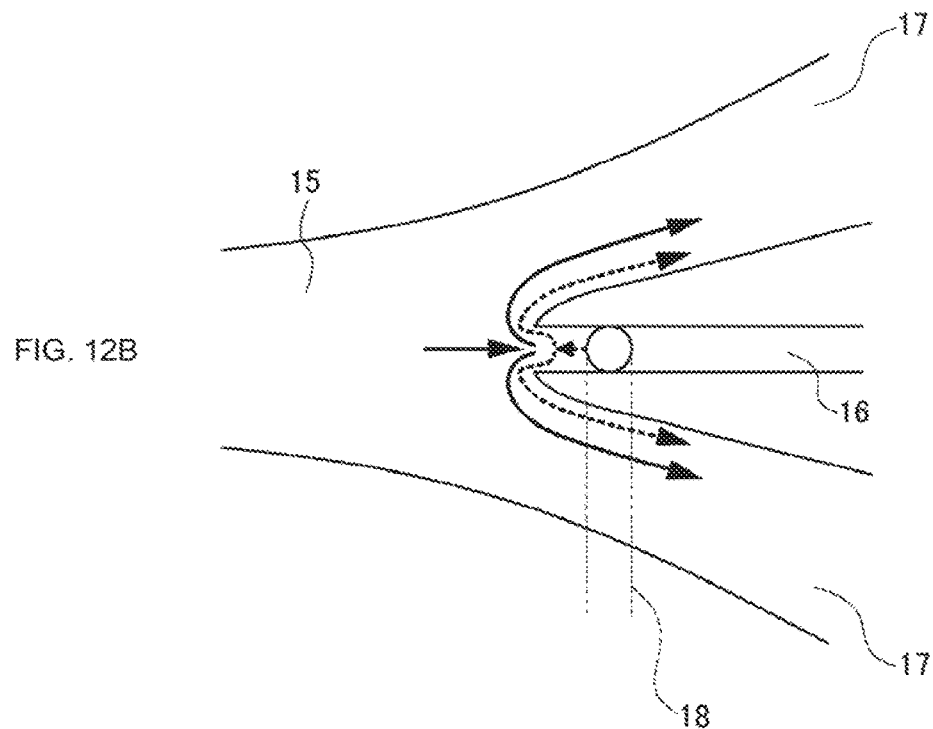

It is preferred that the momentum of the counter flow is set so that it is large enough to completely suppress the entry of the sample fluid and the sheath fluid into the sorting channel 16 from the main channel 15. However, it is acceptable if the counter flow does not completely suppress such entry. As long as the counter flow reduces entry to some extent, the counter flow can contribute to an increase in the speed of the sorting operation. As described above, when the flow of the sample fluid and the sheath fluid that flows along the channel wall from the sorting channel 16 and out the main channel 15 side is produced, this causes the non-target particles, or the sample fluid containing non-target particles, to accumulate. As illustrated in FIG. 12B, if the entry of the sample fluid and the sheath fluid into the sorting channel 16 from the main channel 15 can be reduced by a certain extent, the flow of the sample fluid and the sheath fluid that flows along the channel wall from the sorting channel 16 and out the main channel 15 side which causes accumulation can be suppressed.

It is noted that by suppressing the accumulation at the communication opening 156 of the non-target particles, or a sample fluid containing non-target particles, and the sheath fluid, the target particles and the non-target particles can be prevented from adhering to the channel walls.

Figures 13A, 13B:
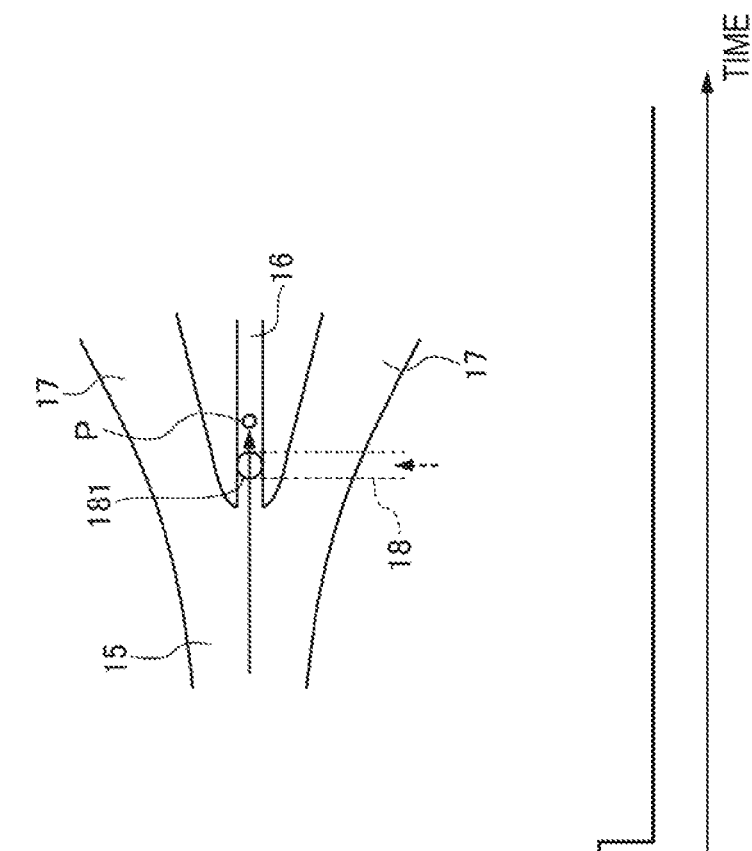
FIGS. 13A and 13B are diagrams illustrating a position where a target particle is drawn in during a sorting operation.

The counter flow is formed at the communication opening 156 even when the target particles are being drawn into the sorting channel 16 (during the sorting operation) (refer to FIG. 13A). Consequently, during the sorting operation, the target particles are drawn into the sorting channel 16 at a drawing pressure that is greater than the counter flow (refer to FIG. 13B). The amount of increase in the volume of the pressure chamber 161 is set so as to be sufficient to generate a drawing pressure greater than the counter flow. The drive unit 23 outputs to the actuator 31 a piezo contraction signal having a voltage width that corresponds to this amount of increase in the volume.

In addition, as illustrated in FIG. 13B, the target particles are drawn into the sorting channel 16 until a position that is past the discharge opening 181. If the drawing into the sorting channel 16 is insufficient, the target particles may flow back out to the main channel 15 due to the counter flow that is formed by the sheath fluid introduced into the sorting channel 16 from the discharge opening 181 by the sheath fluid bypass channel 18.

To sufficiently draw the target particles until a position that is beyond the discharge opening 181, the amount of increase in the volume of the pressure chamber 161 is set to be greater than the flow rate of the counter flow, and the flow rate of the flow of the sample fluid and the sheath fluid that is sucked into the sorting channel 16 from the main channel 15 due to negative pressure is also set to be greater than the flow rate of the counter flow. The drive unit 23 outputs to the actuator 31 a piezo contraction signal having a voltage width that corresponds to this amount of increase in the volume. (Drive Signal)

Figure 14A:
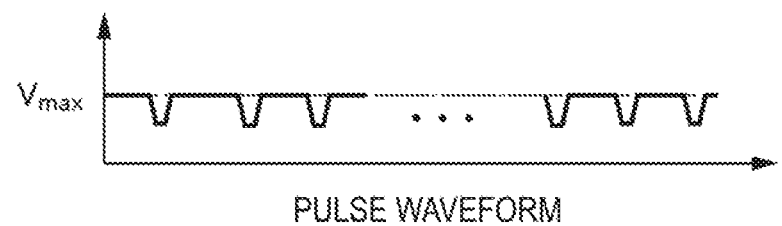
FIGS. 14A, 14B and 14C are diagrams illustrating waveforms of the voltage applied on an actuator 31 from a drive unit 23.
Figure 14B:
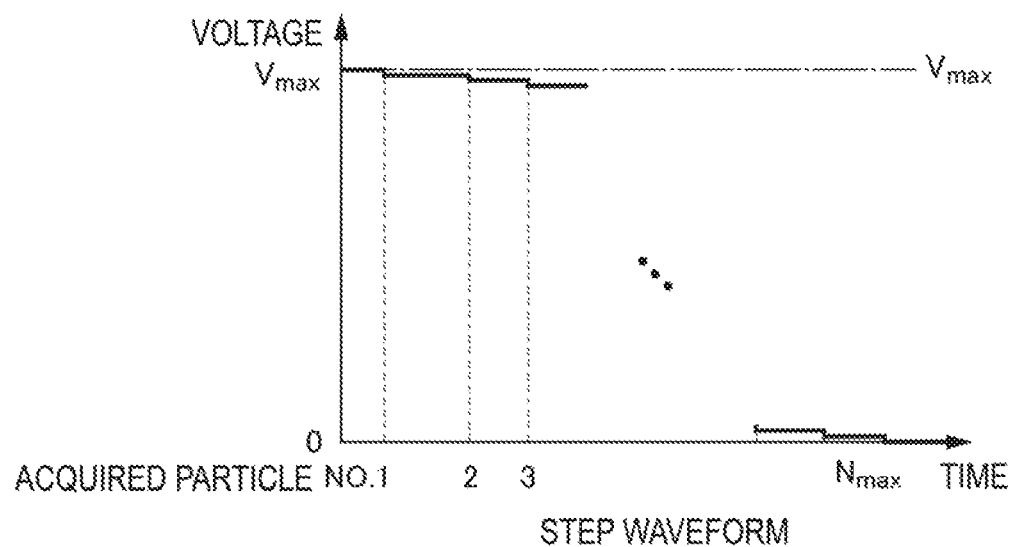
Figure 14C:
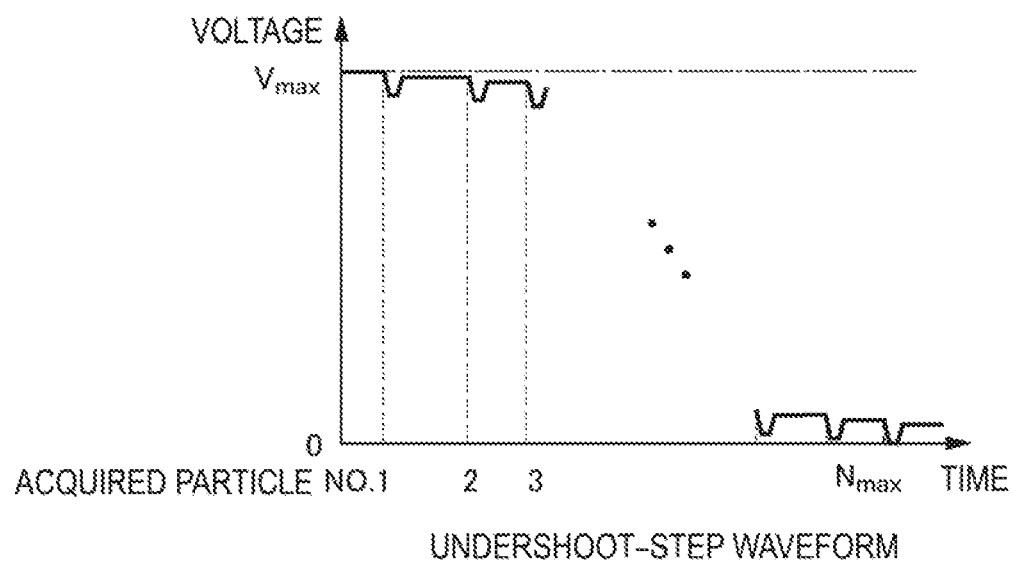

The waveform of the voltage (drive signal when acquiring the target particles) applied on the actuator 31 from the drive unit 23 will now be described with reference to FIGS. 14A, 14B and 14C. The waveform of the voltage applied on the actuator 31 may be any of a "pulse waveform" (FIG. 14A), a "step waveform" (FIG. 14B), or an "undershoot-step waveform" (FIG. 14C).

Here, "undershoot-step waveform" means a waveform obtained by adding to a "step waveform" an undershoot portion in which the voltage value is lower than the step portion. The "undershoot-step waveform" can be said to be a combined wave of the "step waveform" and the "pulse waveform".

The decrease width in the voltage value of the step waveform and the waveform portion in the undershoot-step waveform is set so as to give a sufficient increase in volume to the pressure chamber 161 in order to generate in the sorting channel 16 a drawing pressure that exceeds the counter flow at the communication opening 156. Further, this decrease width is set so as to cause a sufficient increase in the volume of the pressure chamber 161 in order to draw the target particles into the sorting channel 16 until a position that is past the discharge opening 181 due to a negative pressure.

It is preferred that the voltage applied on the actuator 31 is an undershoot-step waveform. With an undershoot-step waveform, the volume of the pressure chamber 161 can be increased immediately after the signal starts to be generated, and a large negative voltage can be generated in the sorting channel 16. Consequently, with an undershoot-step waveform, immediately after starting to draw in the target particles, a response to the increase in the collection volume of the sample fluid and the sheath fluid inlet in the sorting channel 16 from the main channel 15 can be made more quickly, which enables the target particles to be collected more rapidly.

In addition to the conditions for satisfying the step waveform and the undershoot-step waveform, the amplitude of the pulse waveform is set so as to give a sufficient increase in volume to the pressure chamber 161 in order to draw the target particles from the main channel 15 into the pressure chamber 161 and to make the flow of the sample fluid including the target particles and the sheath fluid break away from the channel wall face at the collection opening 162.

Since the pulse waveform and the undershoot-step waveform include a waveform component that causes piezo expansion, the volume of the pressure chamber 161 increases, so that a positive pressure is generated in the sorting channel 16. Further, in the step waveform too, a positive pressure can be generated in the sorting channel 16 due to unexpected fluctuations in the voltage value. As described above, since the target particle P is collected at the back of the pressure chamber 161, the target particle P does not flow back out from the pressure chamber 161 toward the main channel 15 side even if a positive pressure is produced in the sorting channel 16.

As the waveform of the voltage applied on the actuator 31, it is particularly preferred to employ a pulse waveform. For the step waveform and undershoot-step waveform, if the voltage applied on the actuator 31 is zero, the actuator 31 reaches the limit of its movable range, and target particles are incapable of being collected. This means that there is a limit to the maximum number of sortable microparticles. On the other hand, for the pulse waveform, there is no such limit.

Thus, according to the microparticle sorting method according to an embodiment of the present technology, improper entry of the sample fluid and the sheath fluid into the sorting channel 16 from the main channel 15 can be suppressed due to the formation of a counter flow at the communication opening 156 between the main channel 15 and the sorting channel 16. Consequently, in the microparticle sorting method according to an embodiment of the present technology, accumulation of the non-target particles, or a sample fluid containing non-target particles, and the sheath fluid can be prevented, and the sorting operation of the target particles and the non-target particles can be rapidly carried out.

3. Modified Example of the Microparticle Sorting Method According to an Embodiment of the Present Technology In the above-described example, a case was described in which the sheath fluid introduced into the sorting channel 16 from the discharge opening 181 by the sheath fluid bypass channel 18 forms only a counter flow that flows toward the main channel 15 side. In this case, a sorting channel end 19 (refer to FIG. 2) may be a closed end.

Figure 15:
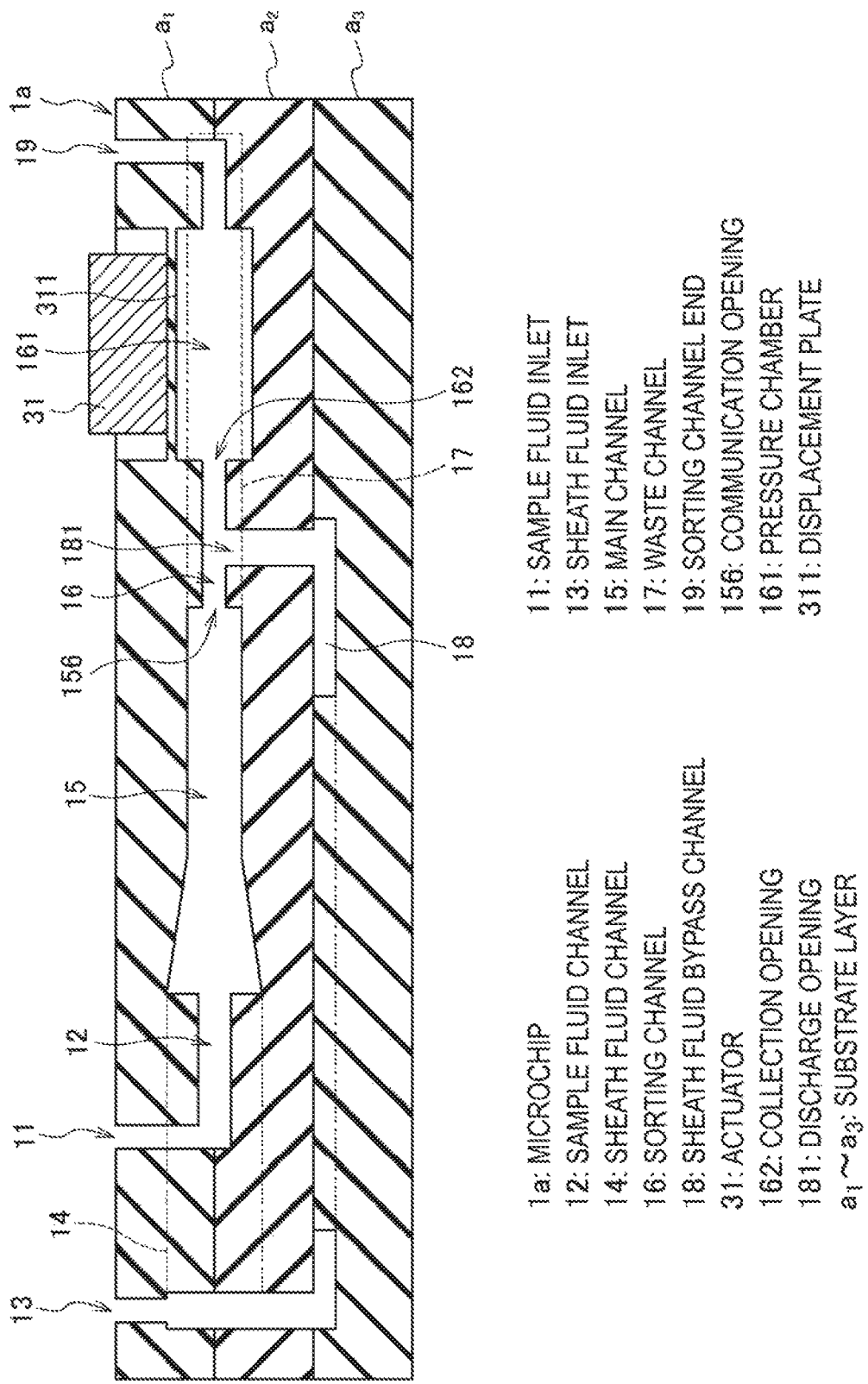

On the other hand, the sorting channel end 19 may also be an open end (refer to FIG. 15). In this case, the sheath fluid introduced into the sorting channel 16 from the discharge opening 181 can be split into a counter flow that flows toward the main channel 15 side and a flow (hereinafter referred to as "forward flow") that flows toward the sorting channel end 19 side.

When control of the voltage applied on the actuator 31 from the drive unit 23 unexpectedly fluctuates, a voltage that causes piezo expansion is applied on the actuator 31, which can produce a positive pressure in the sorting channel 16. Further, a positive pressure can also be produced in the sorting channel 16 when a pressure fluctuation in the main channel 15 and the waste channel 17 occur (especially, a decrease in the back-pressure of the waste channel 17). If such a positive pressure is produced, the target particles that have been collected in the sorting channel 16 may flow back out into the main channel 15.

Due to the formation of the above-described forward flow, the target particles that have been drawn into the sorting channel 16 until a position past the discharge opening 181 are fed further to the back of the sorting channel 16 by the forward flow. Consequently, even if the pressure in the sorting channel 16 is positive, the target particles can be held in the sorting channel 16 without flowing against the forward flow and back out to the main channel 15. Therefore, the control of the drive voltage to the actuator 31 can be carried out under robust conditions.

If the sorting channel end 19 is an open end, the sample fluid including the target particles and the sheath fluid discharged from the sorting channel end 19 are recovered in a container via a tube or the like connected to the sorting channel end 19. To suppress dilution of the recovered target particles, it is preferred that the flow rate of the forward flow is lower than the flow rate of the counter flow. The flow rate ratio between the forward flow and the counter flow can be adjusted by appropriately changing the channel diameter of the sorting channel 16. It is noted that the non-target particles that have flowed to the waste channel 17 may be accumulated in the waste channel 17 or be externally discharged. The waste channels 17 and 17 can also be re-merged so as to configure a single external discharge opening for the non-target particles.

Further, in the above-described example, a case was described in which a counter flow is formed by feeding the sheath fluid introduced from the sheath fluid inlet 13 into the sorting channel 16 by the sheath fluid bypass channel 18. In this case, the counter flow can be formed by a simple chip structure. However, in the microparticle sorting method according to an embodiment of the present technology, as long as a counter flow can be formed at the communication opening 156 between main channel 15 and the sorting channel 16, the fluid for forming the counter flow is not limited to the sheath fluid. In addition, the method for feeding the fluid into the sorting channel 16 is also not limited to employing the sheath fluid bypass channel 18. For example, a feed unit such as a syringe pump may be directly connected to the discharge opening 181.

4. Microparticle Sorting Program

A microparticle sorting program for executing the above-described operations is stored in the drive unit 23 of the above-described microparticle sorting apparatus A.

The program is stored on a hard disk, read into a memory under the control of the CPU and OS, and executes the above-described sorting operation. The program can be recorded on a computer-readable recording medium. The recording medium may be any recording medium as long as it is a computer-readable recording medium. Specifically, a disk-shaped recording medium may be used, such as a flexible disk and a CM-ROM. Further, a tape type recording medium may be used, such as a magnetic tape. In addition, a configuration can also be employed in which a part of the processing may be configured from hardware, such as a DSP (digital signal processor), an ASIC (application specific integrated circuit), a PLD (programing logic device), and a FPGA (field-programmable gate array), and high-speed processing is performed in cooperation with the above-described software program.

It should be understood by those skilled in the art that various modifications, combinations, sub-combinations and alterations may occur depending on design requirements and other factors insofar as they are within the scope of the appended claims or the equivalents thereof.

Additionally, the microparticle sorting method according to the embodiment of the present technology may also be configured as below.

(1) A microparticle sorting method including:

a procedure of collecting a microparticle in a fluid that flows through a main channel in a branch channel that is in communication with the main channel by generating a negative pressure in the branch channel, wherein, in the procedure, a flow of a fluid is formed that flows toward a side of the main channel from a side of the branch channel at a communication opening between the main channel and the branch channel.

(2) The microparticle sorting method according to (1), wherein, in the procedure, the flow is formed by introducing the fluid into the branch channel from an introduction opening positioned near the communication opening in the branch channel.

(3) The microparticle sorting method according to (2), wherein, in the procedure, a flow rate of the fluid that is sucked into the branch channel from the main channel due to negative pressure is greater than a flow rate of the fluid introduced into the branch channel from the introduction opening and fed toward the communication opening.

(4) The microparticle sorting method according to (2) or (3), wherein, in the procedure, the microparticle in the main channel is collected from the communication opening to a position that is past the introduction opening of the branch channel.

(5) The microparticle sorting method according to any one of (1) to (4), wherein the flow is maintained before and after the procedure.

(6) The microparticle sorting method according to any one of (2) to (5), wherein, in the procedure, the fluid introduced into the branch channel from the introduction opening is split into a counter flow that flows toward the communication opening and a forward flow that flows in an opposite direction.

(7) The microparticle sorting method according to any one of (1) to (6), wherein, in the procedure, the negative pressure is generated by an actuator applying a force that deforms an inner space of the branch channel to cause a volume of the inner space to increase.

(8) The microparticle sorting method according to any one of (1) to (7), wherein, in the procedure, a change in the negative pressure having a pulse waveform, a step waveform, or an undershoot-step waveform is produced in the branch channel. Additionally, the microchip for sorting microparticles according to the embodiment of the present technology may also be configured as below.

(9) A microchip for sorting microparticles, including:

a sample fluid introduction opening into which a sample fluid including a microparticle is introduced;

a sample fluid channel through which the sample fluid introduced from the sample fluid introduction opening flows;

a sheath fluid introduction opening into which a sheath fluid is introduced;

a first sheath fluid channel through which the sheath fluid introduced from the sheath fluid introduction opening flows;

a main channel where the sample fluid channel and the first sheath fluid channel merge;

a branch channel that is in communication with the main channel; and a second sheath fluid channel that connects the sheath fluid introduction opening and a sheath fluid discharge opening that is positioned near a communication opening to the main channel in the branch channel, and that feeds the sheath fluid introduced from the sheath fluid introduction opening into the branch channel from the sheath fluid discharge opening.

(10) The microchip for sorting microparticles according to (9), wherein the second sheath fluid channel is not in communication with the sample fluid channel, the first sheath fluid channel, or the main channel.

(11) The microchip for sorting microparticles according to (9) or (10), wherein an actuator for applying a displacement on a contact surface is arranged in contact with a position corresponding to the branch channel on a surface.

(12) The microchip for sorting microparticles according to (11), wherein a pressure chamber for producing a change in volume due to the displacement is configured in the branch channel.

(13) The microchip for sorting microparticles according to (12), wherein the communication opening, the sheath fluid discharge opening, and the pressure chamber are arranged in the branch channel in order of mention.

(14) The microchip for sorting microparticles according to any one of (9) to (13), further including:
the two first sheath fluid channels,
wherein the sheath fluid introduction opening is provided at a symmetrical center of the two first sheath fluid channels.

(15) The microchip for sorting microparticles according to any one of (9) to (14), wherein an end on an opposite side to the communication opening of the branch channel is an open end.

The present disclosure contains subject matter related to that disclosed in Japanese Priority Patent Application JP 2012-180317 filed in the Japan Patent Office on Aug. 16, 2012, the entire content of which is hereby incorporated by reference.

What is claimed is:

1. A microchip, comprising:
a first fluid channel through which a first fluid flows in a first direction, wherein the first fluid comprises of a plurality of microparticles;
a branch channel in communication with the first fluid channel via a first communication opening;
a switching portion communicated with an actuator to generate a pressure to deflect a selected microparticle of the plurality of microparticles into the branch channel; and
a second fluid channel in communication with the branch channel via a second communication opening in the branch channel, wherein
a second fluid flows from the second fluid channel to the second communication opening, and
the second communication opening is downstream of the first communication opening.

2. The microchip according to claim 1, wherein the switching portion is further configured to:
generate a force based on a change in a voltage applied to the actuator; and
change the pressure in the branch channel based on the force.

3. The microchip according to claim 2, wherein
the actuator is configured to apply a displacement on a surface of the microchip based on the applied voltage, and
the actuator is at a position, corresponding to the branch channel, on the surface of the microchip.

4. The microchip according to claim 1, wherein
the switching portion comprising a pressure chamber configured to communicate with the branch channel, and
the pressure chamber is configured to produce a change in volume of the branch channel.

5. The microchip according to claim 1, wherein at least of a portion of the second fluid flows, in a second direction opposite to the first direction, through the second fluid channel from a side of the branch channel towards a side of the first fluid channel.

6. The microchip according to claim 1, further comprising two sheath fluid channels introduce sheath fluid flow into the first fluid channel to form a laminar flow.

7. The microchip according to claim 6, further comprising a first inlet that communicates with the first fluid channel, a sheath inlet that communicates with the sheath fluid channels, a second inlet that communicates with the second fluid channel.

8. The microchip according to claim 7, wherein the two sheath fluid channels comprise a sheath fluid introduction opening at a symmetrical center of the two sheath fluid channels.

9. The microchip according to claim 1, further comprising a waste fluid channel communicate with the first fluid channel via the first communication opening.

10. The microchip according to claim 1, wherein
the actuator is on a surface of the microchip at a position corresponding to a pressure chamber, and
the pressure chamber is in the branch channel.

11. The microchip according to claim 10, wherein
the surface of the microchip comprises a recess portion at the position corresponding to the pressure chamber, and
the actuator is in the recess portion.

12. The microchip according to claim 1, wherein the actuator is a piezo element.

13. A microparticle sorting device, comprising
an actuator,
a microchip, comprising:
a first fluid channel through which a first fluid flows in a first direction, wherein the first fluid comprises a plurality of microparticles;
a branch channel in communication with the first fluid channel via a first communication opening;
a switching portion communicated with the actuator to generate a pressure to deflect a selected microparticle of the plurality of microparticles into the branch channel; and
a second fluid channel in communication with the branch channel via a second communication opening in the branch channel, wherein
a second fluid flows from the second fluid channel to the second communication opening, and
the second communication opening is downstream of the first communication opening.

14. The microparticle sorting device according to claim 13, further comprising:
a light source configured to irradiate light into the plurality of microparticles; and
a detector configured to detect light emitted from the plurality of microparticles.

* * * * *